(12) United States Patent
Tatemoto et al.

(10) Patent No.: US 9,629,577 B2
(45) Date of Patent: Apr. 25, 2017

(54) BIOLOGICAL INFORMATION MEASUREMENT DEVICE AND BIOLOGICAL INFORMATION MEASUREMENT METHOD USING SAME

(71) Applicant: Panasonic Healthcare Holdings Co., Ltd., Tokyo (JP)

(72) Inventors: Susumu Tatemoto, Ehime (JP); Eriko Yoshioka, Ehime (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 353 days.

(21) Appl. No.: 14/389,214

(22) PCT Filed: Apr. 25, 2013

(86) PCT No.: PCT/JP2013/002808
§ 371 (c)(1),
(2) Date: Sep. 29, 2014

(87) PCT Pub. No.: WO2013/168390
PCT Pub. Date: Nov. 14, 2013

(65) Prior Publication Data
US 2015/0087940 A1     Mar. 26, 2015

(30) Foreign Application Priority Data

May 7, 2012    (JP) ................................ 2012-105725

(51) Int. Cl.
*A61B 5/145*      (2006.01)
*A61B 5/1473*     (2006.01)
(Continued)

(52) U.S. Cl.
CPC ...... *A61B 5/14535* (2013.01); *A61B 5/14517* (2013.01); *A61B 5/14532* (2013.01);
(Continued)

(58) Field of Classification Search
CPC ........... A61B 5/14517; A61B 5/14532; A61B 5/14535; A61B 5/14546; A61B 5/14735; G01N 27/3274; G01N 33/49
See application file for complete search history.

(56) References Cited

U.S. PATENT DOCUMENTS 5,411,029 A * 5/1995 Hirai .................... A61B 5/0452
600/508
5,803,908 A * 9/1998 Steuer ................ A61B 5/14535
600/314

(Continued)

FOREIGN PATENT DOCUMENTS

EP     2 098 857     9/2009
EP     2 306 190     4/2011
(Continued)

*Primary Examiner* — Francis Gray
(74) *Attorney, Agent, or Firm* — Hamre, Schumann, Mueller & Larson, P.C.

(57) ABSTRACT

The present invention relates to a biological information measurement device and a biological information measurement method using the same, and is intended to allow appropriate measurement to be carried out. In the biological information measurement device of the present invention, a control unit 18 is allowed to execute a pre-processing voltage application mode A and a biological information measurement mode C. Furthermore, in the biological information measurement device of the present invention, the hematocrit value of blood is calculated in either the pre-processing voltage application mode A or the biological information measurement mode C, and according to the hematocrit value thus calculated, the duration for applying a measuring voltage upon and after the calculation of the hematocrit value is modified.

10 Claims, 8 Drawing Sheets

(51) Int. Cl.
  *G01N 27/327* (2006.01)
  *G01N 33/49* (2006.01)
(52) U.S. Cl.
  CPC ...... *A61B 5/14546* (2013.01); *A61B 5/14735* (2013.01); *G01N 27/3274* (2013.01); *G01N 33/49* (2013.01)

(56) References Cited

U.S. PATENT DOCUMENTS

| | | | | |
|---|---|---|---|---|
| 8,137,529 | B2* | 3/2012 | Huang | C12Q 1/006 205/775 |
| 8,308,935 | B2* | 11/2012 | Chen | A61B 5/14532 204/403.02 |
| 8,709,232 | B2* | 4/2014 | Matzinger | G01N 27/3274 204/403.01 |
| 2005/0067301 | A1 | 3/2005 | Morita et al. | |
| 2007/0131565 | A1 | 6/2007 | Fujiwara et al. | |
| 2007/0138026 | A1 | 6/2007 | Fujiwara et al. | |
| 2009/0152127 | A1 | 6/2009 | Kaimori et al. | |
| 2010/0187132 | A1* | 7/2010 | Alden | G01N 27/4163 205/790.5 |
| 2010/0283488 | A1* | 11/2010 | Nakamura | G01N 27/327 324/692 |
| 2011/0203942 | A1* | 8/2011 | Uchiyama | G01N 27/3274 205/782 |
| 2013/0105334 | A1* | 5/2013 | Nakamura | G01N 27/327 205/792 |
| 2013/0220836 | A1* | 8/2013 | Kermani | A61B 5/14532 205/782 |
| 2014/0224672 | A1* | 8/2014 | Hsu | C12Q 1/001 205/777.5 |
| 2015/0068926 | A1* | 3/2015 | Ainger | G01N 27/3271 205/792 |

FOREIGN PATENT DOCUMENTS

| | | |
|---|---|---|
| JP | 2005-147990 | 6/2005 |
| JP | 2011-033638 | 2/2011 |
| JP | 2011-075362 | 4/2011 |
| JP | 2011-164116 | 8/2011 |
| WO | 03/044513 | 5/2003 |
| WO | 2005/054840 | 6/2005 |
| WO | 2007/032286 | 3/2007 |
| WO | 2009/119118 | 10/2009 |
| WO | 2010/061629 | 6/2010 |

* cited by examiner

BIOLOGICAL INFORMATION MEASUREMENT DEVICE AND BIOLOGICAL INFORMATION MEASUREMENT METHOD USING SAME

TECHNICAL FIELD

The present invention relates to a biological information measurement device for measuring, for example, a blood glucose level, and a biological information measurement method using the same.

BACKGROUND ART

Conventionally, a biological information measurement device, to which a biosensor having a first electrode and a second electrode, a reagent portion provided between the first and second electrodes, and a guide portion for guiding blood into the reagent portion is attached, had the following configuration.

That is, it had a configuration including a first input terminal, to which the first electrode is connected, a second input terminal, to which the second electrode is connected, a voltage applying unit for applying a voltage to the first input terminal and the second input terminal, a determination unit connected to the first input terminal and the second input terminal, a control unit connected to the determination unit and the voltage applying unit, and a display unit connected to the control unit (for example, Patent Document 1 below).

PRIOR ART DOCUMENT

Patent Document

[Patent Document 1] WO2007/032286

DISCLOSURE OF INVENTION

Problem to be Solved by the Invention

In the conventional example described above, the control unit was configured to execute a pre-processing voltage application mode, in which a pre-processing voltage is applied to the first input terminal and the second input terminal, a voltage application pause mode, in which after the pre-processing voltage application mode, the voltage application to the first input terminal and the second input terminal is paused, and a biological information measurement mode, in which after the voltage application pause mode, a measuring voltage is applied to the first input terminal and the second input terminal to measure biological information.

Such a conventional example has had a problem in that appropriate measurement cannot be carried out.

That is, in the above-mentioned conventional example, since the value of the blood glucose level to be measured varies depending on the hematocrit value of the blood, the duration of the biological information measurement mode is set to be longer in order to reduce the variation.

Specifically, higher hematocrit values result in a large variation in the value of the blood glucose level to be measured. In the conventional example, the duration of the biological information measurement mode is set to be long in order to reduce the variation.

However, the hematocrit values of many subjects whose blood glucose levels are measured are not so high. When even for such subjects, the biological information measurement mode takes a long time, it cannot be considered as appropriate measurement for subjects who wish to finish the measurement as quickly as possible.

However, when the duration of the biological information measurement mode is reduced uniformly, the blood glucose level of a subject who has a high hematocrit value varies greatly. Thus, also in this case, appropriate measurement cannot be carried out.

Therefore, it is an object of the present invention to allow appropriate measurement to be carried out.

Means for Solving Problem

In order to attain this object, the present invention provides a configuration, in which the control unit calculates the hematocrit value of the blood in either the pre-processing voltage application mode or the biological information measurement mode and modifies, according to the hematocrit value calculated, the duration for applying a measuring voltage to the first input terminal and the second input terminal upon and after the calculation of the hematocrit value, and thereby attains the desired object.

As described above, it is an object of the present invention to provide a biological information measurement device, to which a biosensor is attached, the biosensor having a first electrode and a second electrode, a reagent portion provided between the first electrode and the second electrode, and a guide portion for guiding blood to the reagent portion, wherein the biological information measurement device includes:

a first input terminal, to which the first electrode is connected, and a second input terminal, to which the second electrode is connected, a voltage applying unit for applying a voltage to the first input terminal and the second input terminal, and a control unit connected to the voltage applying unit, the control unit is configured to execute:

a pre-processing voltage application mode, in which the voltage applying unit applies a pre-processing voltage to the first input terminal and the second input terminal, and a biological information measurement mode, in which after the pre-processing voltage application mode, the voltage applying unit applies a measuring voltage to the first input terminal and the second input terminal to measure biological information, and the control unit has a configuration, in which the hematocrit value of the blood is calculated in either the pre-processing voltage application mode or the biological information measurement mode, and according to the hematocrit value thus calculated, the duration for applying the measuring voltage to the first input terminal and the second input terminal upon and after the calculation of the hematocrit value is modified.

Furthermore, it is an object of the present invention to provide a biological information measurement device, to which a biosensor is attached, the biosensor having a first electrode and a second electrode, a reagent portion provided between the first electrode and the second electrode, and a guide portion for guiding blood to the reagent portion, wherein the biological information measurement device includes:

a first input terminal, to which the first electrode is connected, and a second input terminal, to which the second electrode is connected, a voltage applying unit for applying a voltage to the first input terminal and the second input terminal, and a control unit connected to the voltage applying unit,
the control unit is configured to execute:
a pre-processing voltage application mode, in which the voltage applying unit applies a pre-processing voltage to the first input terminal and the second input terminal,
a voltage application pause mode, in which after the pre-processing voltage application mode, the voltage applying unit pauses the voltage application to the first input terminal and the second input terminal, and
a biological information measurement mode, in which after the voltage application pause mode, the voltage applying unit applies a measuring voltage to the first input terminal and the second input terminal to measure biological information, and
the control unit has a configuration, in which the hematocrit value of the blood is calculated in an early stage of the biological information measurement mode and according to the hematocrit value thus calculated, the duration for applying the measuring voltage upon and after the calculation of the hematocrit value is modified.

Effects of the Invention

As described above, the present invention provides a configuration, in which the control unit calculates the hematocrit value of the blood in either the pre-processing voltage application mode or the biological information measurement mode and modifies, according to the hematocrit value thus calculated, the duration for applying the measuring voltage upon and after the calculation of the hematocrit value. Thus, appropriate measurement can be carried out.

In other words, when the hematocrit value calculated is higher than a predetermined value, the variation in the biological information to be measured increases. Therefore, in order to reduce the variation, the duration for applying the measuring voltage is increased. In this way, the variation in the biological information to be measured can be reduced and as a result, appropriate measurement can be carried out.

Furthermore, when the hematocrit value calculated is lower than the predetermined value, the duration for applying the measuring voltage is reduced. In this way, the measurement time can be shortened and also in this case, appropriate measurement can be carried out.

DESCRIPTION OF THE INVENTION

Hereinafter, an embodiment of the present invention is described using accompanying drawings.

[Embodiment 1]

Figure 1:
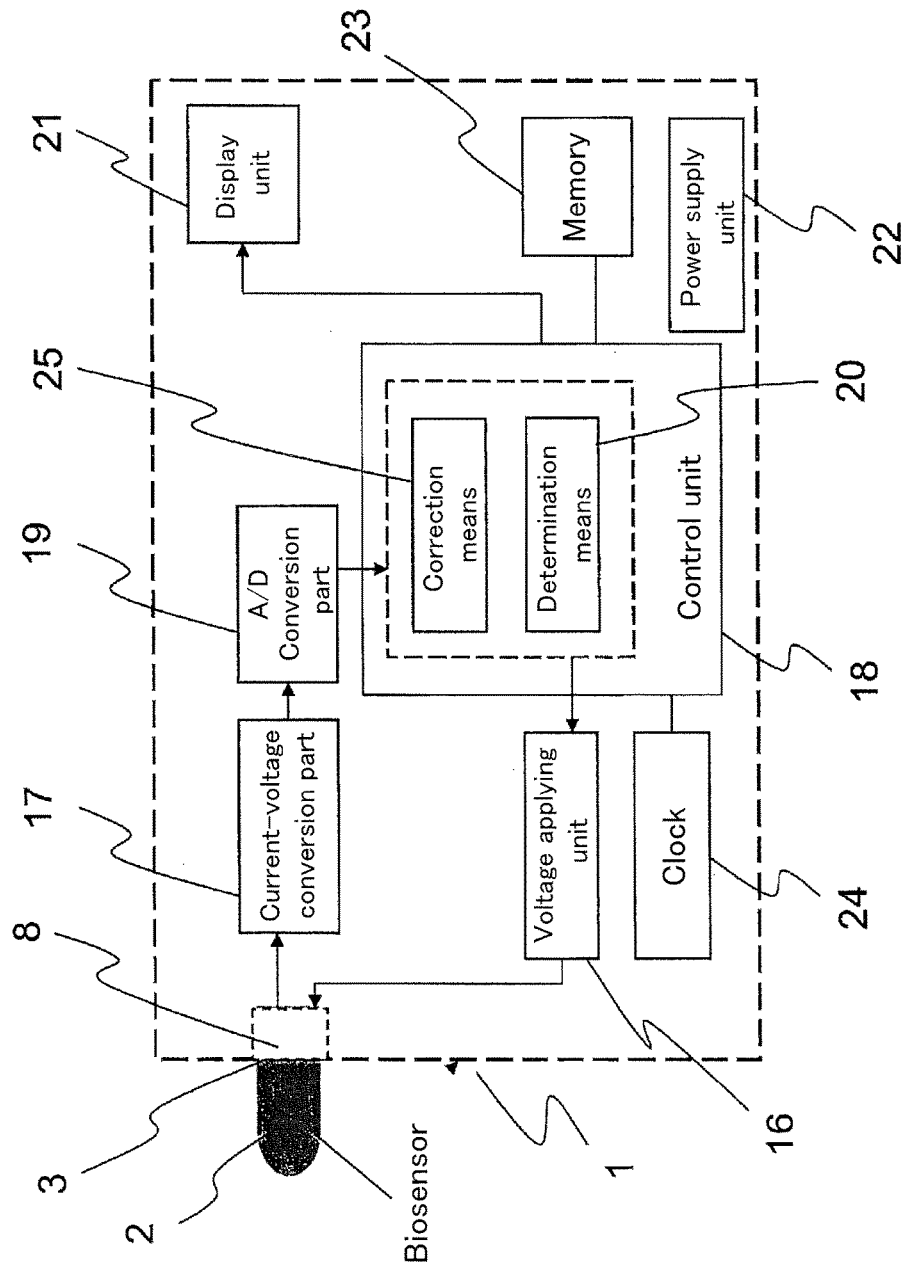
FIG. 1 is an electrical block diagram of a biological information measurement device according to an embodiment of the present invention.

FIG. 1 shows an electrical block diagram of a biological information measurement device according to an embodiment of the present invention. FIG. 2A is an exploded perspective view of a biosensor that is used for the biological information measurement device according to the embodiment of the present invention. FIG. 2B is a cross-sectional view of the biosensor that is used for the biological information measurement device according to the embodiment of the present invention. As shown in FIG. 1, in this biological information measurement device, a body case 1 is provided with an insertion opening 3 for a biosensor 2 on one end thereof.

As in an example shown in FIG. 2A, the biosensor 2 is formed, with a blood component measurement working electrode 5, a blood component measurement counter electrode 6, and a blood component introduction detection electrode 7 being arranged, on a rectangular-shaped insulating substrate 4, opposed to one another at a predetermined interval. Examples of the biological information to be measured by the biological information measurement device of the present invention include a glucose value, a lactic acid value, a uric acid level, a bilirubin level, and a cholesterol level. Furthermore, examples of the biological sample that is used for obtaining such biological information include blood, urine, and sweat. This biosensor 2 is an example in the case of using blood as a biological sample.

In this biosensor 2, the blood component measurement working electrode 5, the blood component measurement counter electrode 6, and the blood component introduction detection electrode 7 each come into contact with an input terminal portion 8 shown in FIG. 1 on one end side (the right end side in FIG. 2) of the insulating substrate 4, and thereby the biosensor 2 is electrically connected to the biological information measurement device.

Furthermore, in this biosensor 2, a reagent portion 9 is arranged on an electrode part formed of the blood component measurement working electrode 5, the blood component measurement counter electrode 6, and the blood component introduction detection electrode 7.

Moreover, in this biosensor 2, a reagent 10 is placed on the reagent portion 9. The reagent 10 contains oxidoreductase, such as glucose dehydrogenase, and a mediator (an electron carrier) and selectively contains, as optional components, a polymeric material, an enzyme stabilizer, a crystal homogenizer, etc. In this biosensor 2, a cover 12 is placed over the insulating substrate 4 and the reagent 10 with a spacer 11 interposed therebetween, with one end of the insulating substrate 4 being left.

In the spacer 11 of the biosensor 2, a blood supply path (an example of a guide portion) 13 for introducing blood is formed. This blood supply path 13 extends from the other end side (the left end side in FIG. 2) of the biosensor 2 to above the reagent 10, and the other end side that is open to the outside forms a blood supply port 14.

Furthermore, the blood component measurement working electrode 5, the blood component measurement counter electrode 6, and the blood component introduction detection electrode 7 extend to the one end side (the right end side in FIG. 2) of the biosensor 2, and parts of the blood component measurement working electrode 5, the blood component measurement counter electrode 6, and the blood component introduction detection electrode 7 are exposed without being covered by the cover 12.

The one end sides of these respective electrodes are connected at the input terminal portion 8 shown in FIG. 1.

Specifically, in this biosensor 2, the blood component measurement working electrode 5 is connected to a first input terminal (not shown in the drawings) of the input terminal portion 8, the blood component measurement counter electrode 6 is connected to a second input terminal (not shown in the drawings) of the input terminal portion 8, and further the blood component introduction detection electrode 7 is connected to a third input terminal (not shown in the drawings) of the input terminal portion 8.

Figure 2:
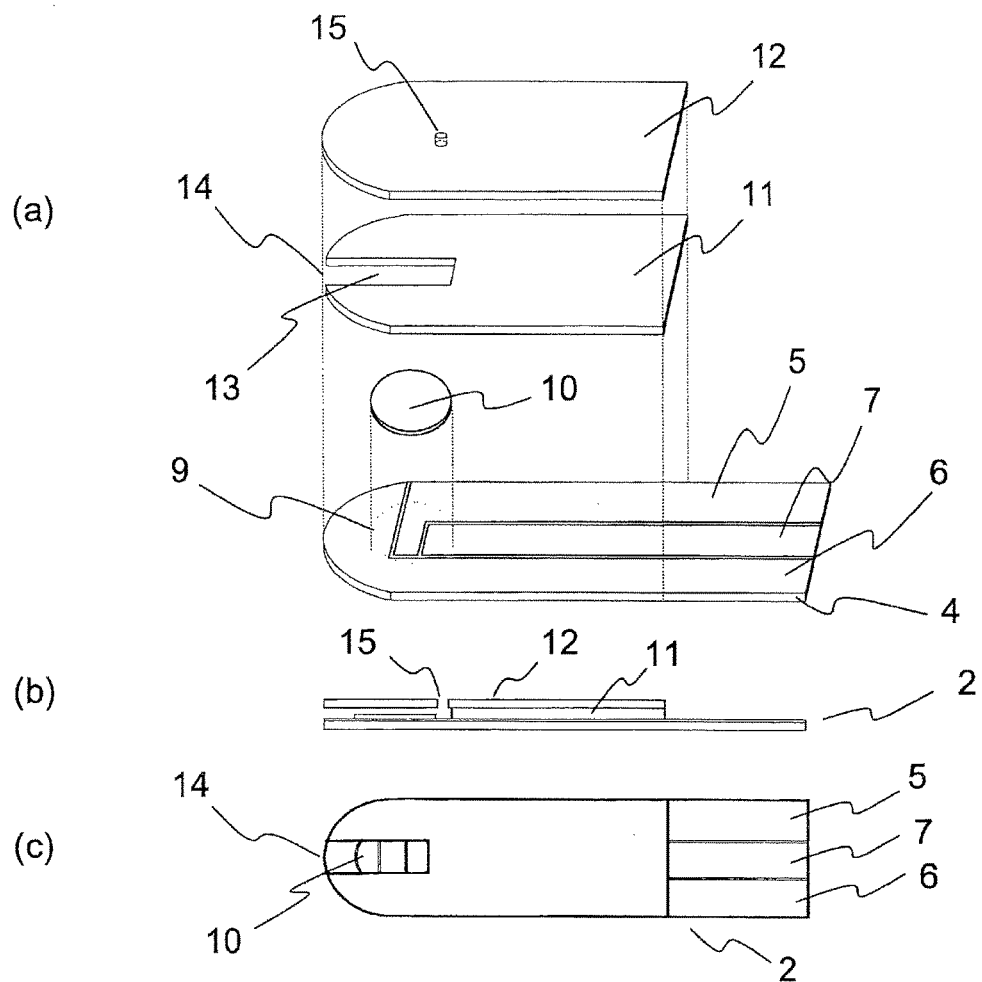
FIG. 2A is an exploded perspective view of a biosensor that is used for the biological information measurement device according to the embodiment of the present invention.
FIG. 2B is a cross-sectional view of the biosensor that is used for the biological information measurement device according to the embodiment of the present invention.
FIG. 2C is a plan view of the biological information measurement device according to the embodiment of the present invention.

Furthermore, as is understood also from FIG. 2, in this biosensor 2, the blood component measurement counter electrode 6 is arranged closest to the blood supply port 14, and then the blood component measurement working electrode 5 and the blood component introduction detection electrode 7 are arranged sequentially.

That is, in this biosensor 2, the blood component measurement counter electrode (an example of a first electrode) 6, the blood component measurement working electrode (an example of a second electrode) 5, and the blood component introduction detection electrode 7 are arranged sequentially from the blood supply port 14 side.

The cover 12 of the biosensor 2 has an air hole 15 formed therein for promoting the capillary phenomenon when a drop of blood is applied to the blood supply port 14 and for allowing the blood to permeate to the blood component introduction detection electrode 8.

Next, the configuration of the biosensor 2 is described in further details.

In the present invention, the material of the insulating substrate 4 is not particularly limited. Examples thereof that can be used include polyethylene terephthalate (PET), polycarbonate (PC), polyimide (PI), polyethylene (PE), polypropylene (PP), polystyrene (PS), polyvinyl chloride (PVC), polyoxymethylene (POM), monomer cast nylon (MC), polybutylene terephthalate (PBT), methacrylic resin (PMMA), ABS resin (ABS), and glass. Among them, polyethylene terephthalate (PET), polycarbonate (PC), and polyimide (PI) are preferable and polyethylene terephthalate (PET) is more preferable.

Furthermore, the size of the insulating substrate 4 is not particularly limited. It has, for example, a total length of 5 to 100 mm, a width of 2 to 50 mm, and a thickness of 0.05 to 2 mm, preferably a total length of 7 to 50 mm, a width of 3 to 20 mm, and a thickness of 0.1 to 1 mm, and further preferably a total length of 10 to 30 mm, a width of 3 to 10 mm, and a thickness of 0.1 to 0.6 mm.

Each electrode arranged on the insulating substrate 4 can be formed by using, for example, gold, platinum, or palladium as a material, forming a conductive layer by a sputtering method or a vapor deposition method, and then processing it into a specific electrode pattern with a laser. Examples of the laser that can be used include a YAG laser, a $CO_2$ laser, and an excimer laser. The electrode pattern is not limited to the one disclosed in the present invention and it can be any electrode pattern as long as it allows the effects of the present invention to be obtained. The electrodes of the biosensor 2 that is used in the present invention may be coated with a polymeric material for the purposes of, for example, preventing impurities from adhering to them and preventing them from being oxidized. The surfaces of the electrodes can be coated as follows. For example, a solution of a polymeric material is prepared and this is dropped or applied onto the electrode surfaces, which then is dried. Examples of the drying method include natural drying, air drying, hot air drying, and heat drying.

The electron carrier of the biosensor 2 to be used is not particularly limited. Examples thereof include ferricyanide, p-benzoquinone, p-benzoquinone derivatives, phenazine methosulfate, methylene blue, ferrocene, and ferrocene derivatives. Among them, ferricyanide is preferable and potassium ferricyanide is more preferable. The amount of the electron carrier to be mixed is not particularly limited but is, for example, 0.1 to 1000 mM, preferably 1 to 500 mM, and more preferably 10 to 200 mM per measurement or per biosensor.

The oxidoreductase to be used in the present invention may be selected suitably depending on the type of the biological information. Examples of the oxidoreductase include glucose oxidase, lactate oxidase, cholesterol oxidase, bilirubin oxidase, glucose dehydrogenase, and lactate dehydrogenase. The amount of the oxidoreductase is, for example, 0.01 to 100 U, preferably 0.05 to 10 U, and more preferably 0.1 to 5 U per sensor or per measurement. Among them, glucose is preferable as the biological information, and in this case, oxidoreductase is preferably glucose oxidase or glucose dehydrogenase.

In the present invention, the reagent 10 can be formed as follows. For example, 0.1~5.0 U/sensor of flavin adenosine dinucleotide dependent glucose dehydrogenase (FAD-GDH), 10 to 200 mM of potassium ferricyanide, 1 to 50 mM of maltitol, and 20 to 200 mM of taurine are added to 0.01 to 2.0 wt % carboxymethyl cellulose (CMC) solution to be dissolved therein and thereby a reagent solution is prepared. This is dropped onto the electrodes of the insulating substrate 4 and then is dried.

Next, in the present invention, the material of the spacer 11 is not particularly limited but, for example, a similar material to that of the insulating substrate 4 can be used. Furthermore, the size of the spacer 11 is not particularly limited. The spacer 11 has, for example, a total length of 5 to 100 mm, a width of 2 to 50 mm, and a thickness of 0.01 to 1 mm, preferably a total length of 7 to 50 mm, a width of 3 to 20 mm, and a thickness of 0.05 to 0.5 mm, and more preferably a total length of 10 to 30 mm, a width of 3 to 10 mm, and a thickness of 0.05 to 0.25 mm. The spacer 11 has an I-shaped cut part formed to serve as the blood supply path 13 for introducing blood.

Furthermore, in the present invention, the material of the cover 12 is not particularly limited but, for example, a similar material to that of the insulating substrate 4 can be used. It is further preferable that the portion corresponding to the ceiling portion of the blood supply path 13 of the cover 12 be subjected to a hydrophilic treatment. Examples of the method used for the hydrophilic treatment include a method in which a surfactant is applied and a method in which a hydrophilic functional group such as a hydroxyl group, a carbonyl group, or a carboxyl group is introduced into the cover 12 surface by, for example, a plasma treatment. The size of the cover 12 is not particularly limited and the cover 12 has, for example, a total length of 5 to 100 mm, a width of 3 to 50 mm, and a thickness of 0.01 to 0.5 mm, preferably a total length of 10 to 50 mm, a width of 3 to 20 mm, and a thickness of 0.05 to 0.25 mm, and more preferably a total length of 15 to 30 mm, a width of 5 to 10 mm, and a thickness of 0.05 to 0.1 mm. Preferably, an air hole 15 is formed in the cover 12. The shape thereof is, for example, round, oval, or polygonal. The air hole 15 has, for example, a maximum diameter of 0.01 to 10 mm, preferably a maximum diameter of 0.05 to 5 mm, and more preferably a maximum diameter of 0.1 to 2 mm. The air hole 15 may be formed by, for example, making a hole with a laser or a drill, or may be formed using a mold that allows an air vent part to be formed when the cover 12 is formed. Next, as shown in FIG. 2, the biosensor 2 can be produced by stacking the insulating substrate 4, the spacer 11, and the cover 12 in this order and forming them into one body. In forming them into one body, the aforementioned three members may be attached together with an adhesive or may be heat-sealed. Examples of the adhesive that can be used include an epoxy adhesive, an acrylic adhesive, a polyurethane adhesive, a thermosetting adhesive (such as a hot-melt adhesive), and a UV curable adhesive.

Returning to FIG. 1 to continue the description, a voltage applying unit 16 for applying a voltage and a current-voltage conversion part 17 are connected to the input terminal portion 8 of the biological information measurement device according to the embodiment of the present invention.

A voltage is applied to the voltage applying unit 16 from a control unit 18. This voltage is applied, for a predetermined duration, to a desired electrode selected from the blood component measurement working electrode 5, the blood component measurement counter electrode 6, and the blood component introduction detection electrode 7 of the biosensor 2 through the input terminal portion 8. By this voltage application, the current that flows between the electrodes in the biosensor 2 is converted to a voltage in the current-voltage conversion part 17. After that, the voltage is digitally converted in an A/D conversion part 19 and the voltage thus digitally converted is compared to a threshold value by a determination means 20.

In a display unit 21 connected to the control unit 18, a blood glucose level detected in the biosensor 2 and a determination result provided by the determination means 20 are displayed.

In FIG. 1, numeral 22 indicates a power supply unit, which is used for supplying power to the respective parts described above. Numeral 23 indicates a memory unit that is provided with a calibration curve and a calibration table that are prepared beforehand from ambient temperature and tables including hematocrit values, the voltage to be applied and duration for application in measuring glucose, etc.

Furthermore, a clock 24 is connected to the control unit 18, and the control unit 18 is configured to make use of the time of the clock 24 to execute various control operations.

Furthermore, a correction means 25 is provided inside of the control unit 18. It corrects the measured blood glucose level according to the hematocrit value and thereby increases the accuracy of measuring the blood glucose level.

Figure 3:
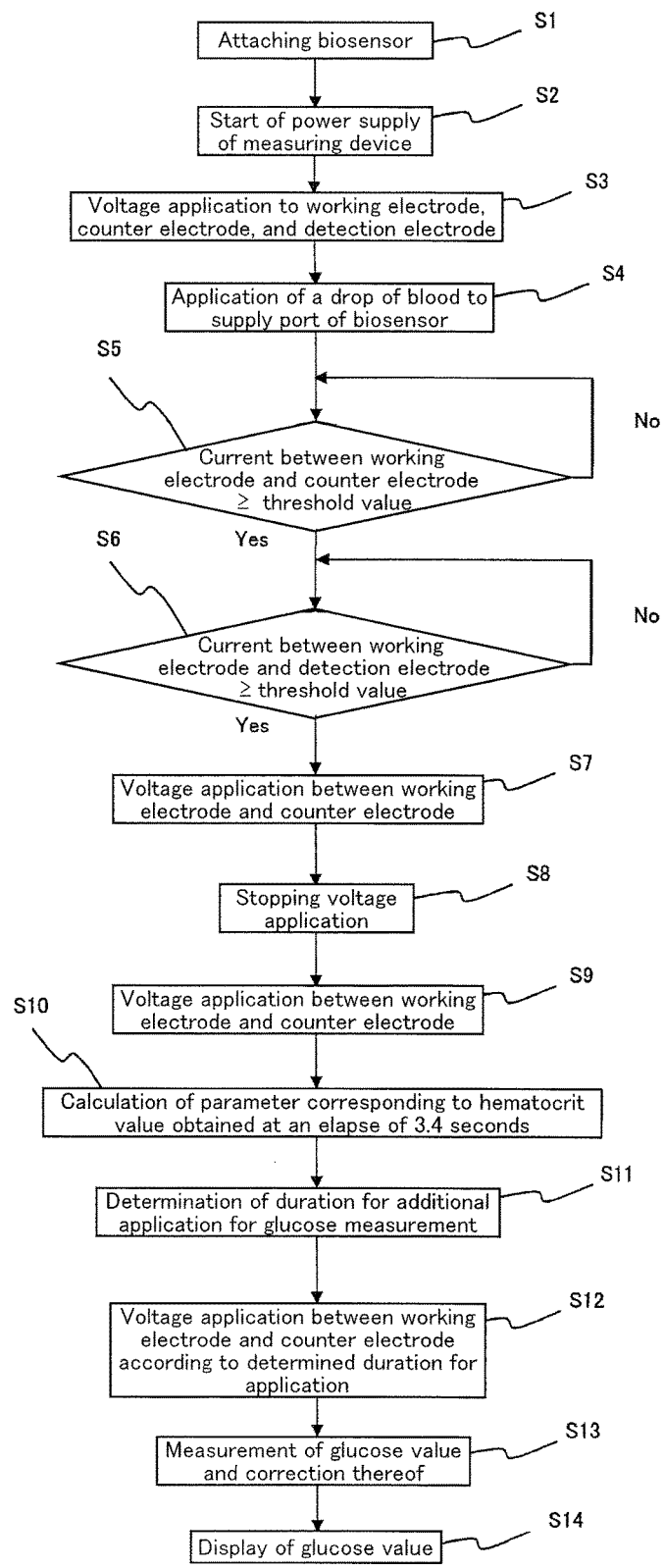
FIG. 3 is an operation flow chart of the biological information measurement device according to the embodiment of the present invention.

In the configuration described above, when the blood glucose level is measured, first, the biosensor 2 shown in FIG. 2, which is stored in plurality inside a drying container (not shown in the drawings) before being used, is taken out one by one from the drying container whenever the glucose value (the blood glucose level, biological information) is measured, and the biosensor 2 is attached to the insertion opening 3 of the body case 1 as shown in FIG. 1 (S1 "Attaching Biosensor" in FIG. 3).

Then, the control unit 18 recognizes that the biosensor 2 has been attached to the input terminal portion 8. In order to allow the measurement operation to start, the switch (not shown in the drawings) is brought into the on state and thereby power is supplied to each part from the power supply unit 22 (S2 "Start of Power Supply of Measuring Device" shown in FIG. 3). In this state, no drop of blood of a user has been applied to the blood supply port 15 part.

Upon starting the measurement operation, the control unit 18 allows the voltage applying unit 16 to operate to apply a voltage to each of the blood component measurement working electrode 5, the blood component measurement counter electrode 6, and the blood component introduction detection electrode 7 of the biosensor 2 (S3 "Voltage Application to Working Electrode, Counter Electrode, and Detection Electrode" shown in FIG. 3). In the present embodiment, the voltage to be applied to each of the blood component measurement working electrode 5, the blood component measurement counter electrode 6, and the blood component introduction detection electrode 7 is, for example, 0.5 V.

Next, the subject exudes blood by pricking, for example, a finger with a lancet or the like and in that state, a drop of blood is applied to the blood supply port 14 of the biosensor 2 (S4 "Application of A Drop of Blood to Supply Port of Biosensor" shown in FIG. 3).

The drop of blood thus applied advances inwards through the blood supply path 13 by the capillary phenomenon. Then, a current starts to flow between the blood component measurement working electrode 5 and the blood component measurement counter electrode 6, the current is converted to a voltage in the current-voltage conversion part 16, which thereafter is subjected to A/D conversion in the A/D conversion part 19, and then determination is carried out by the determination means 20 of the control unit 18.

Specifically, the control unit 18 measures the value of the current flowing between the blood component measurement working electrode 5 and the blood component measurement counter electrode 6 and determines whether the current is equal to or higher than the threshold value (for example, 10 mV). When the voltage value proportional to the value of the current flowing between the blood component measurement working electrode 5 and the blood component measurement counter electrode 6 is lower than the threshold value, the determination means 20 of the control unit 18 determines that the drop of blood that has been applied has not fully permeated into the reagent 10, and this comparison is repeated until the value of the current flowing between the blood component measurement working electrode 5 and the blood component measurement counter electrode 6 becomes equal to or higher than the threshold value. That is, the control unit 18 determines whether the blood has reached the blood component measurement working electrode 5 (S5 "Current between Working Electrode and Counter Electrode≥Threshold Value" shown in FIG. 3).

After the blood has reached the blood component measurement working electrode 5, subsequently, the value of the current flowing between the blood component measurement working electrode 5 and the blood component introduction detection electrode 7 is measured and whether the current is equal to or higher than the threshold value (for example, 10 mV) is determined in the same manner. When it is lower than the threshold value, it is determined that the drop of blood applied has not fully permeated into the reagent 10 and the blood component introduction detection electrode 7, and this comparison is repeated until the value of the current becomes equal to or higher than the threshold value. That is, whether the blood has reached the blood component introduction detection electrode 7 is determined (S6 "Current between Working Electrode and Detection Electrode≥Threshold Value" shown in FIG. 3").

When the value of the current flowing therebetween becomes equal to or higher than the threshold value in S5 and then S6 shown in FIG. 3, the determination means 20 of the control unit 18 determines that the blood has been introduced to an extent that allows measurement to fully be carried out. When this state is entered, the control unit 18 applies the voltage shown in FIG. 4 between the blood component measurement working electrode 5 and the blood component measurement counter electrode 6 for a predetermined duration, for example, 0.5 to 4.0 seconds (2.0 seconds in the present embodiment) (S7 "Voltage Application between Working Electrode and Counter Electrode", S8 "Stopping Voltage Application", and S9 "Voltage Application between Working Electrode and Counter Electrode" shown in FIG. 3).

Figure 4:
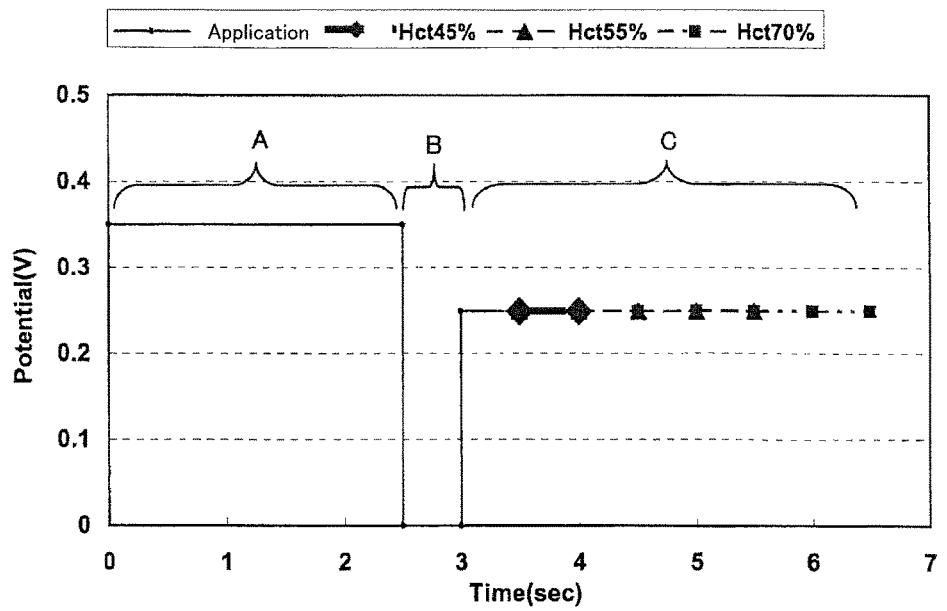
FIG. 4 is a graph showing the state of the voltage to be applied with time in the biological information measurement device according to the embodiment of the present invention.

In the present embodiment, the control unit 18 is allowed to execute a pre-processing voltage application mode A, a voltage application stop mode B, and a biological information measurement mode C shown in FIG. 4. FIG. 4 is a graph showing the state of the voltage to be applied with time in the biological information measurement device according to the embodiment of the present invention.

In the present embodiment, in the pre-processing voltage application mode A, the voltage shown in FIG. 4 is applied as a pre-processing voltage between a first input terminal and a second input terminal (not shown in the drawings) of the input terminal portion 8, that is, between the blood component measurement working electrode 5 and the blood component measurement counter electrode 6.

In this embodiment, in the voltage application stop mode B, after the pre-processing voltage application mode A, the voltage application to the first input terminal (not shown in the drawings) of the input terminal portion 8 shown in FIG. 1 and the second input terminal (not shown in the drawings) of the input terminal portion 8, that is, to the blood component measurement counter electrode 6 and the blood component measurement working electrode 5, is stopped for about 0.1 to 5.0 seconds (1.0 second in the present embodiment). During this period of time when the voltage application is stopped, glucose contained in the blood and oxidoreductase react with each other for a certain period of time.

In this embodiment, in the biological information measurement mode C, after the voltage application stop mode B, a voltage is applied to the first input terminal (not shown in the drawings) of the input terminal portion 8 and the second input terminal (not shown in the drawings) of the input terminal portion 8, that is, to the blood component measurement counter electrode 6 and the blood component measurement working electrode 5, and thereby biological information (a blood glucose level) is measured. In the biological information measurement mode C, an electron carrier in a reduced state, which was produced on the blood component measurement working electrode 5 by the enzyme reaction in the voltage application stop mode B, is oxidized, the oxidation current then is detected, and thereby the blood glucose level is measured.

The characteristic point in the present embodiment is that the control unit 18 calculates the hematocrit value of the blood in an early stage of the biological information measurement mode C and according to the hematocrit value thus calculated, the duration for applying a measuring voltage upon and after the calculation of the hematocrit value is modified.

That is, the control unit 18 calculates the parameter correspond to the hematocrit value in an early stage (for example, at an elapse of 3.4 seconds) of the biological information measurement mode C and modifies the duration for applying a measuring voltage upon and after the calculation of the hematocrit value (S10 "Calculation of Parameter Corresponding to Hematocrit Value Obtained at An Elapse of 3.4 Seconds" and S11 "Determination of Duration for Additional Application for Glucose Measurement" shown in FIG. 3).

Specifically, in order to calculate the hematocrit value, the control unit 18 calculates a plurality of parameters (x1, x2, x3 . . . , x10) from measured current values obtained at a plurality of predetermined times in the pre-processing voltage application mode A and the biological information measurement mode C, and then inputs them into a multiple regression equation (for example, Formula 1 below) to calculate the hematocrit value.

$$y=ax1+bx2+cx3 \ldots +kx10+1 \quad \text{(Formula 1)}$$

(wherein y denotes a hematocrit value, x1, x2, x3 . . . , x10 denote parameters, and a, b, c, . . . k denote coefficients).

(With respect to such calculation of the hematocrit value, see JP 2005-147990 A)

According to the hematocrit value calculated in Formula 1, the control unit 18 modifies the duration for applying a measuring voltage (between the blood component measurement counter electrode 6 and the blood component measurement working electrode 5) upon and after the calculation of the hematocrit value in the biological information measurement mode C (S12 "Voltage Application between Working Electrode and Counter Electrode According to Determined Duration for Application" shown in FIG. 3).

Figure 5:
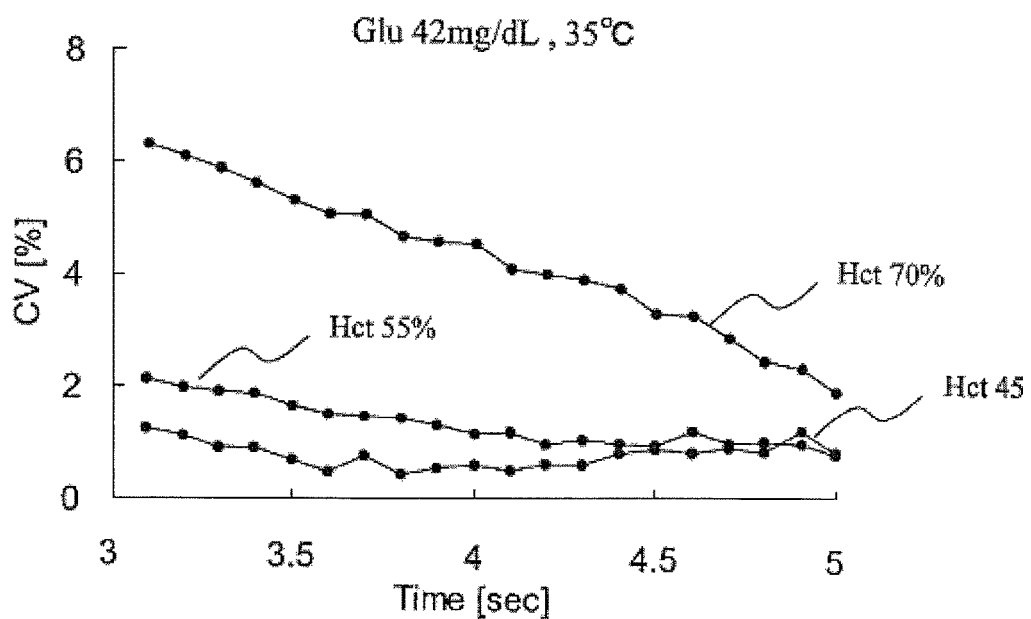
FIG. 5 is a graph showing the variations in biological information obtained with different hematocrit values by the biological information measurement device according to the embodiment of the present invention.

FIG. 5 shows how the blood glucose level to be measured varies depending on the hematocrit value. As is apparent from FIG. 5, with the hematocrit value being 45% or 55%, even when the duration for applying the voltage between the blood component measurement counter electrode 6 and the blood component measurement working electrode 5 in the biological information measurement mode C varies, the variations are suppressed to be small.

However, it became clear that with the hematocrit value exceeding 55%, for example, the hematocrit value being 70%, in the biological information measurement mode C, a longer duration for applying the voltage between the blood component measurement counter electrode 6 and the blood component measurement working electrode 5 results in smaller variations in the measurement of the blood glucose level.

Therefore, in the present embodiment, in the case where the hematocrit value is 45%, the duration for applying a measuring voltage (between the blood component measurement counter electrode 6 and the blood component measurement working electrode 5) upon and after the calculation of the hematocrit value in the biological information measurement mode C is 0.1 sec, that is, the voltage applied to the blood component measurement counter electrode 6 and the blood component measurement working electrode 5 in the biological information measurement mode C is stopped at an elapse of 3.5 seconds shown in FIG. 5. In that state, the control unit 18 calculates the blood glucose level (biological information).

The blood glucose level (biological information) calculated above is subjected to a conventionally known temperature correction (S13 "Measurement of Glucose Value and Correction Thereof" shown in FIG. 3).

In other words, since the enzyme reaction used in measuring the blood glucose level is affected by the ambient temperature, such a temperature correction is carried out.

Then, the blood glucose level determined, with the correction having been carried out as described above, is displayed on the display unit 21 as the final blood glucose level (S14 "Display of Glucose Value" shown in FIG. 3).

On the other hand, in the case where the hematocrit value is 55%, the duration for applying a measuring voltage (between the blood component measurement counter electrode 6 and the blood component measurement working electrode 5) upon and after the calculation of the hematocrit value in the biological information measurement mode C is 0.6 sec, that is, the voltage applied to the blood component measurement counter electrode 6 and the blood component measurement working electrode 5 in the biological information measurement mode C is stopped at an elapse of 4.0 seconds shown in FIG. 5. In that state, the control unit 18 calculates the blood glucose level (biological information).

The blood glucose level (biological information) calculated above is subjected to a conventionally known temperature correction (S13 "Measurement of Glucose Value and Correction Thereof" shown in FIG. 3).

In other words, since the enzyme reaction used in measuring the blood glucose level is affected by the ambient temperature, such a temperature correction is carried out.

Then, the blood glucose level determined, with the correction having been carried out as described above, is displayed on the display unit 21 as the final blood glucose level (S14 "Display of Glucose Value" shown in FIG. 3).

Furthermore, in the case where the hematocrit value is 70%, the duration for applying a measuring voltage (between the blood component measurement counter electrode 6 and the blood component measurement working electrode 5) upon and after the calculation of the hematocrit value in the biological information measurement mode C is 1.6 seconds, that is, the voltage applied to the blood component measurement counter electrode 6 and the blood component measurement working electrode 5 in the biological information measurement mode C is stopped at an elapse of 5.0 seconds shown in FIG. 5. In that state, the control unit 18 calculates the blood glucose level (biological information).

The blood glucose level (biological information) calculated above is subjected to a conventionally known temperature correction (S13 "Measurement of Glucose Value and Correction Thereof" shown in FIG. 3).

In other words, since the enzyme reaction used in measuring the blood glucose level is affected by the ambient temperature, such a temperature correction is carried out.

Then, the blood glucose level determined, with the correction having been carried out as described above, is displayed on the display unit 21 as the final blood glucose level (S14 "Display of Glucose Value" shown in FIG. 3).

The present embodiment is characterized in that the control unit 18 calculates the hematocrit value of the blood and according to the hematocrit value thus calculated, the duration for applying a measuring voltage in the biological information measurement mode C is modified. As a result, the blood glucose level to be displayed on the display unit 21 is measured appropriately.

In other words, when the hematocrit value calculated is higher than the predetermined value (for example, a hematocrit value of 70% shown in FIG. 5), the variation in biological information to be measured increases. Therefore, in order to reduce the variation, the duration for applying a measuring voltage is increased, so that the variation in biological information to be measured can be reduced. As a result, appropriate measurement can be carried out.

Furthermore, when the hematocrit value calculated is lower than the predetermined value (for example, the hematocrit values of 45% and 55% shown in FIG. 5), the duration for applying a measuring voltage is reduced, so that the measurement time is shortened, which also allows appropriate measurement to be carried out.

Such measurement of the blood glucose level is carried out, with a drop of blood being applied to the biosensor 2. Depending on the subject, some people do not like to show such blood to other people. Therefore, also for such people, it is preferable since the measurement can be completed quickly.

In the embodiment described above, the pre-processing voltage application mode A, the voltage application stop mode B, and the biological information measurement mode C are allowed to be executed in this order. However, the voltage application stop mode B may be aborted and the biological information measurement mode C may be allowed to be executed following the pre-processing voltage application mode A.

In this case, in the pre-processing voltage application mode A, for example, at the final point thereof, the hematocrit value of the blood is calculated and according to the hematocrit value thus calculated, the duration for applying a measuring voltage upon and after the calculation of the hematocrit value is modified.

That is, the following configuration may be employed: after the hematocrit value is calculated in such a manner, the mode to be executed thereafter is the biological information measurement mode C, and the duration for applying a measuring voltage in this biological information measurement mode C is modified.

Also in this case, for example, when the hematocrit value calculated exceeds 55%, the control unit 18 increases the duration for applying a measuring voltage in the biological information measurement mode C as compared to the case where the hematocrit value is 55% or lower.

Next, examples of the present invention are described.

EXAMPLE 1

A biosensor having a configuration shown in FIG. 1 and a biological information measurement device shown in FIG. 2 are produced. In the sensor, a reagent solution prepared by dissolving potassium ferricyanide and taurine in a CMC aqueous solution was dropped and then was allowed to be dried. Thus, a reagent 10 was formed. Three types of blood samples each contained glucose in an amount of 42 mg/dL, and the amounts of hematocrit contained therein were 45%, 55%, and 75%, respectively. With respect to these three blood samples, with the sensor described above, the current flowing in the electrodes of the sensor was measured at 35° C. under the conditions including the duration for application shown in FIG. 6 and an applied voltage of 300 mV (n=6). The results are shown in FIG. 7. FIG. 7 is a graph showing the variations with time in sensitivity difference (CV, %) with respect to the applied voltage.

Figure 6:
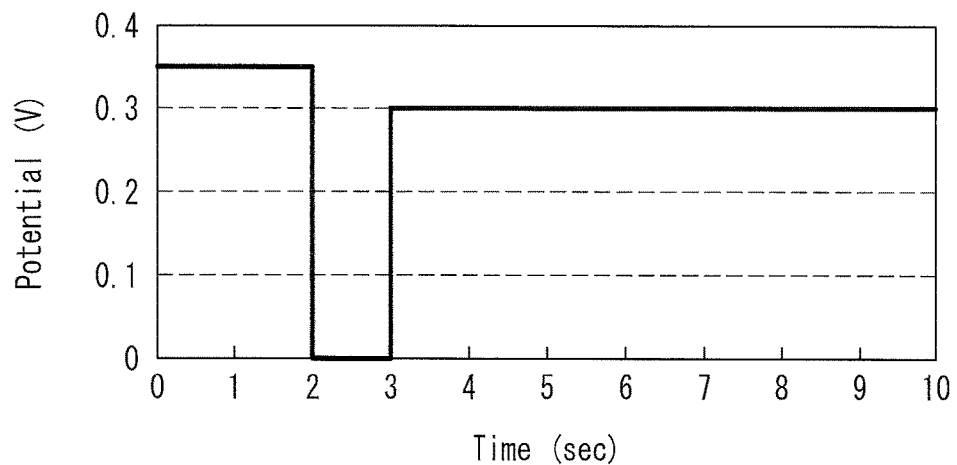
FIG. 6 is a graph showing the state of the voltage to be applied with time in a biological information measurement device according to Example 1.
Figure 7:
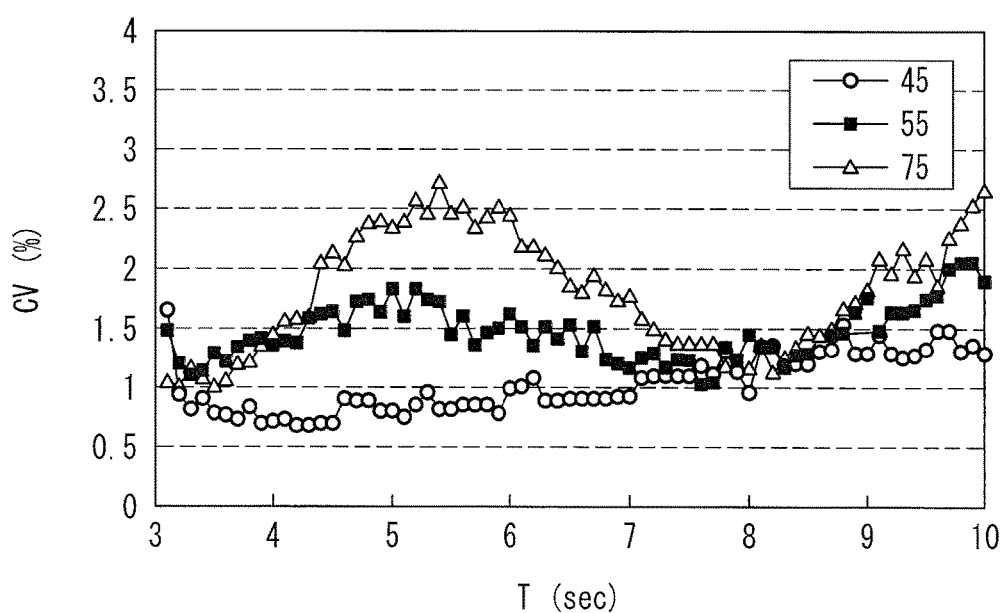
FIG. 7 is a graph showing the variations in biological information obtained with different hematocrit values by the biological information measurement device according to Example 1.

As shown in FIG. 6, in the case of using this sensor, when the hematocrit value is 45%, the duration for applying a measuring voltage in the biological information measurement mode C is 1 second, that is, the voltage applied to the blood component measurement counter electrode 6 and the blood component measurement working electrode 5 in the biological information measurement mode C is stopped at an elapse of 4 seconds shown in FIG. 6. In that state, the control unit 18 calculates the blood glucose level (biological information). Furthermore, when the hematocrit value is 55%, the duration for applying a measuring voltage in the biological information measurement mode C is 5 seconds, that is, the voltage applied to the blood component measurement counter electrode 6 and the blood component measurement working electrode 5 in the biological information measurement mode C is stopped at an elapse of 8 seconds shown in FIG. 6. In that state, the control unit 18 calculates the blood glucose level (biological information). Moreover, when the hematocrit value is 70%, the duration for applying a measuring voltage in the biological information measurement mode C is 5 seconds, that is, the voltage applied to the blood component measurement counter electrode 6 and the blood component measurement working electrode 5 in the biological information measurement mode C is stopped at an elapse of 8 seconds shown in FIG. 6. In that state, the control unit 18 calculates the blood glucose level (biological information). Then, these blood glucose levels were subjected to a conventionally known temperature correction. The blood glucose levels thus obtained each were displayed on the display unit 21 as the final blood glucose level.

Example 1 is characterized in that the control unit 18 calculated the hematocrit value of the blood and according to the hematocrit value thus calculated, the duration for applying a measuring voltage in the biological information measurement mode C was modified. As a result, as shown in FIG. 7, the variations in the blood glucose levels displayed on the display unit 21 were reduced. Furthermore, as shown in FIG. 7, in the case of samples with different hematocrit values, even when the duration for applying a measuring voltage between the blood component measurement counter electrode 6 and the blood component measurement working electrode 5 in the biological information measurement mode C varied, the variations were suppressed to be small, which was confirmed.

EXAMPLE 2

Figure 8:
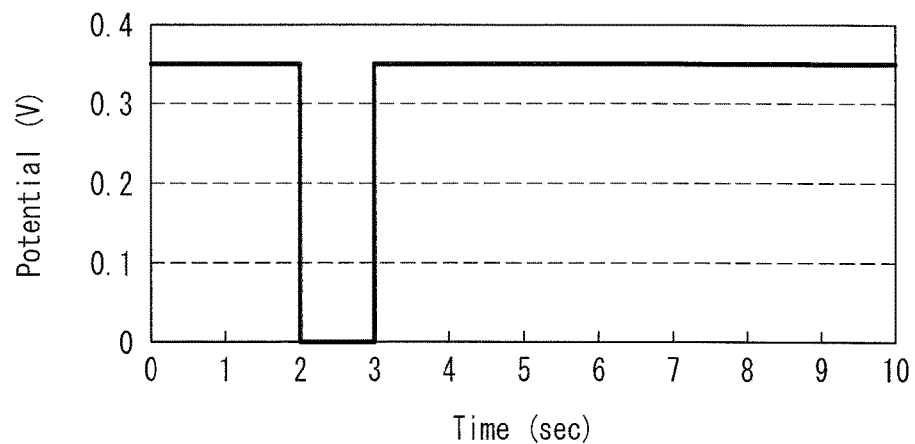
FIG. 8 is a graph showing the state of the voltage to be applied with time in a biological information measurement device according to Example 2.
Figure 9:
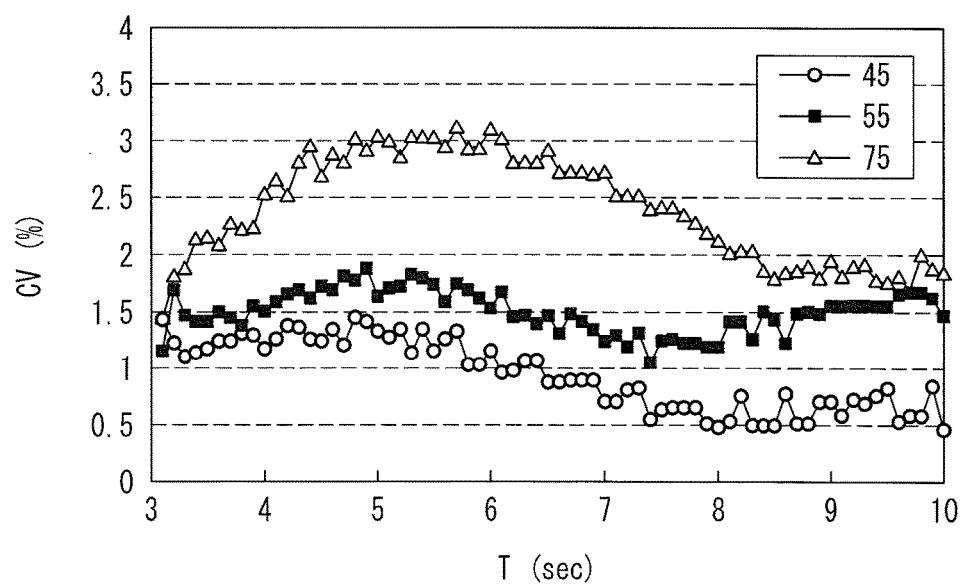
FIG. 9 is a graph showing the variations in biological information obtained with different hematocrit values by the biological information measurement device according to Example 2.

This example was carried out in the same manner as in Example 1 except that with the sensor described above, the current flowing in the electrodes of the sensor was measured at 35° C. under the conditions including the duration for application shown in FIG. 8 and an applied voltage of 350 mV (n=6). The results are shown in FIG. 9. FIG. 9 is a graph showing the variations with time in sensitivity difference (CV, %) with respect to the applied voltage.

As shown in FIG. 8, in the case of using this sensor, when the hematocrit value is 45%, the duration for applying a measuring voltage in the biological information measurement mode C is 4 seconds, that is, the voltage applied to the blood component measurement counter electrode 6 and the blood component measurement working electrode 5 in the biological information measurement mode C is stopped at an elapse of 7 seconds shown in FIG. 8. In that state, the control unit 18 calculates the blood glucose level (biological information). Furthermore, when the hematocrit value is 55%, the duration for applying a measuring voltage in the biological information measurement mode C is 5 seconds, that is, the voltage applied to the blood component measurement counter electrode 6 and the blood component measurement working electrode 5 in the biological information measurement mode C is stopped at an elapse of 8 seconds shown in FIG. 8. In that state, the control unit 18 calculates the blood glucose level (biological information). Moreover, when the hematocrit value is 70%, the duration for applying a measuring voltage in the biological information measurement mode C is 6 seconds, that is, the voltage applied to the blood component measurement counter electrode 6 and the blood component measurement working electrode 5 in the biological information measurement mode C is stopped at an elapse of 9 seconds shown in FIG. 8. In that state, the control unit 18 calculates the blood glucose level (biological information). Then, these blood glucose levels were subjected to a conventionally known temperature correction. The blood glucose levels thus obtained each were displayed on the display unit 21 as the final blood glucose level.

Example 2 is characterized in that the control unit 18 calculated the hematocrit value of the blood and according to the hematocrit value thus calculated, the duration for applying a measuring voltage in the biological information measurement mode C was modified. As a result, as shown in FIG. 9, the variations in the blood glucose levels displayed on the display unit 21 were reduced. Furthermore, as shown in FIG. 9, in the case of samples with different hematocrit values, even when the duration for applying a measuring voltage between the blood component measurement counter electrode 6 and the blood component measurement working electrode 5 in the biological information measurement mode C varied, the variations were suppressed to be small, which was confirmed.

EXAMPLE 3

Figure 10:
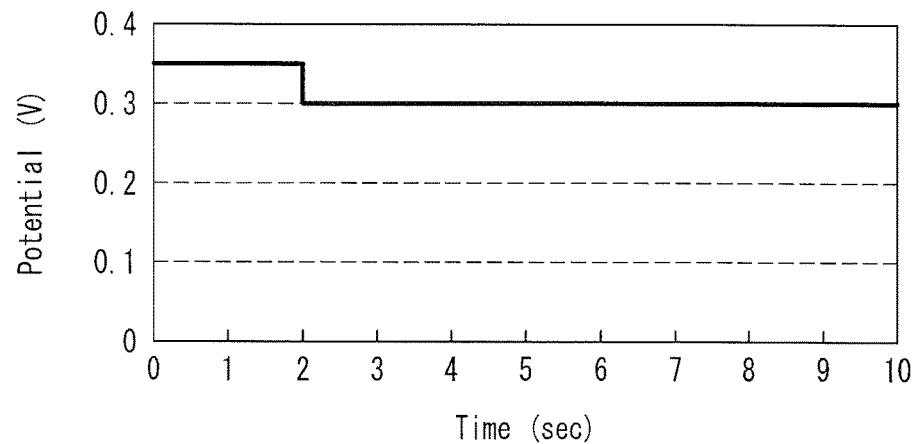
FIG. 10 is a graph showing the state of the voltage to be applied with time in a biological information measurement device according to Example 3.
Figure 11:
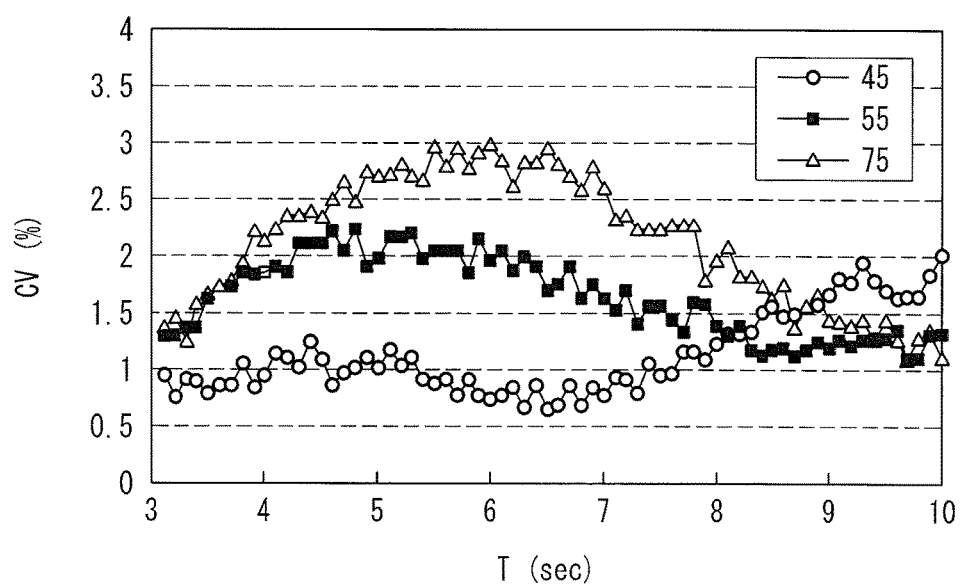
FIG. 11 is a graph showing the variations in biological information obtained with different hematocrit values by the biological information measurement device according to Example 3.

This example was carried out in the same manner as in Example 1 except that with the sensor described above, the current flowing in the electrodes of the sensor was measured at 35° C. under the conditions including the duration for application shown in FIG. 10 and an applied voltage of 300 mV (n=6). The results are shown in FIG. 11. FIG. 11 is a graph showing the variations with time in sensitivity difference (CV, %) with respect to the applied voltage.

As shown in FIG. 10, in the case of using this sensor, when the hematocrit value is 45%, the duration for applying a measuring voltage in the biological information measurement mode C is 1 second, that is, the voltage applied to the blood component measurement counter electrode 6 and the blood component measurement working electrode 5 in the biological information measurement mode C is stopped at an elapse of 4 seconds shown in FIG. 10. In that state, the control unit 18 calculates the blood glucose level (biological information). Furthermore, when the hematocrit value is 55%, the duration for applying a measuring voltage in the biological information measurement mode C is 5 seconds, that is, the voltage applied to the blood component measurement counter electrode 6 and the blood component measurement working electrode 5 in the biological information measurement mode C is stopped at an elapse of 8 seconds shown in FIG. 10. In that state, the control unit 18 calculates the blood glucose level (biological information). Moreover, when the hematocrit value is 70%, the duration for applying a measuring voltage in the biological information measurement mode C is 7 seconds, that is, the voltage applied to the blood component measurement counter electrode 6 and the blood component measurement working electrode 5 in the biological information measurement mode C is stopped at an elapse of 10 seconds shown in FIG. 10. In that state, the control unit 18 calculates the blood glucose level (biological information). Then, these blood glucose levels were subjected to a conventionally known temperature correction. The blood glucose levels thus obtained each were displayed on the display unit 21 as the final blood glucose level.

Example 3 is characterized in that the control unit 18 calculated the hematocrit value of the blood and according to the hematocrit value thus calculated, the duration for applying a measuring voltage in the biological information measurement mode C was modified. As a result, as shown in FIG. 11, the variations in the blood glucose levels displayed on the display unit 21 were reduced. Furthermore, as shown in FIG. 11, in the case of samples with different hematocrit values, even when the duration for applying a measuring voltage between the blood component measurement counter electrode 6 and the blood component measurement working electrode 5 in the biological information measurement mode C varied, the variations were suppressed to be small, which was confirmed.

EXAMPLE 4

Figure 12:
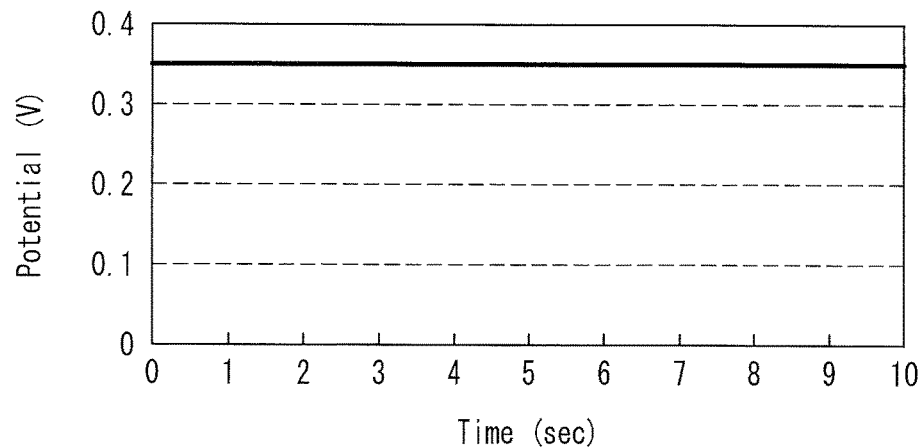
FIG. 12 is a graph showing the state of the voltage to be applied with time in a biological information measurement device according to Example 4.
Figure 13:
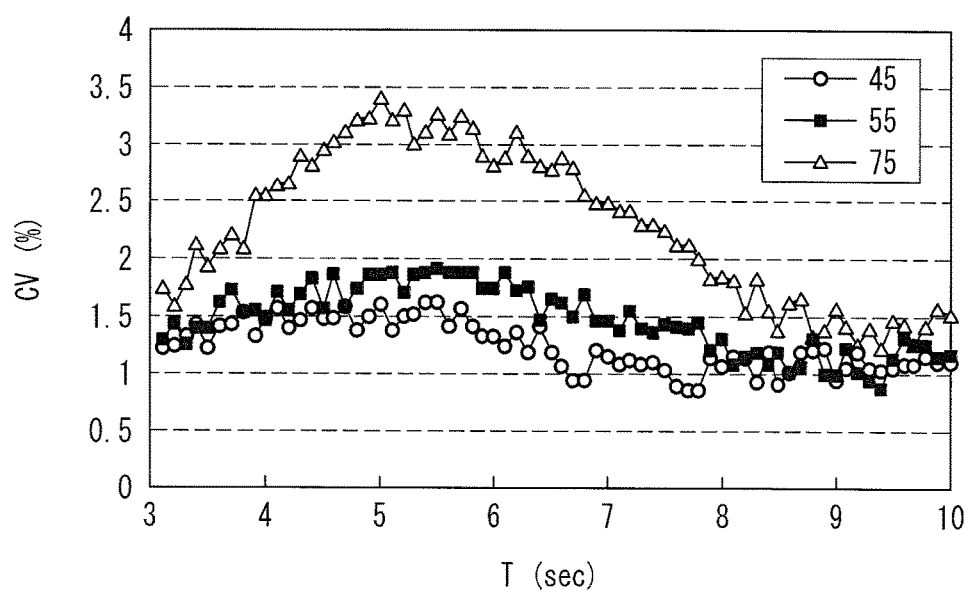
FIG. 13 is a graph showing the variations in biological information obtained with different hematocrit values by the biological information measurement device according to Example 4.

This example was carried out in the same manner as in Example 1 except that with the sensor described above, the current flowing in the electrodes of the sensor was measured at 35° C. under the conditions including the duration for application shown in FIG. 12 and an applied voltage of 350 mV (n=6). The results are shown in FIG. 13. FIG. 13 is a graph showing the variations with time in sensitivity difference (CV, %) with respect to the applied voltage.

As shown in FIG. 12, in the case of using this sensor, when the hematocrit value is 45%, the duration for applying a measuring voltage in the biological information measurement mode C is 2 seconds, that is, the voltage applied to the blood component measurement counter electrode 6 and the blood component measurement working electrode 5 in the biological information measurement mode C is stopped at an elapse of 5 seconds shown in FIG. 12. In that state, the control unit 18 calculates the blood glucose level (biological information). Furthermore, when the hematocrit value is 55%, the duration for applying a measuring voltage in the biological information measurement mode C is 5 seconds, that is, the voltage applied to the blood component measurement counter electrode 6 and the blood component measurement working electrode 5 in the biological information measurement mode C is stopped at an elapse of 8 seconds shown in FIG. 12. In that state, the control unit 18 calculates the blood glucose level (biological information). Moreover, when the hematocrit value is 70%, the duration for applying a measuring voltage in the biological information measurement mode C is 6 seconds, that is, the voltage applied to the blood component measurement counter electrode 6 and the blood component measurement working electrode 5 in the biological information measurement mode C is stopped at an elapse of 9 seconds shown in FIG. 12. In that state, the control unit 18 calculates the blood glucose level (biological information). Then, these blood glucose levels were subjected to a conventionally known temperature correction. The blood glucose levels thus obtained each were displayed on the display unit 21 as the final blood glucose level.

Example 4 is characterized in that the control unit 18 calculated the hematocrit value of the blood and according to the hematocrit value thus calculated, the duration for applying a measuring voltage in the biological information measurement mode C was modified. As a result, as shown in FIG. 13, the variations in the blood glucose levels displayed on the display unit 21 were reduced. Furthermore, as shown in FIG. 13, in the case of samples with different hematocrit values, even when the duration for applying a measuring voltage between the blood component measurement counter electrode 6 and the blood component measurement working electrode 5 in the biological information measurement mode C varied, the variations were suppressed to be small, which was confirmed.

INDUSTRIAL APPLICABILITY

As described above, the present invention has a configuration, in which the control unit calculates the hematocrit value of the blood in either the pre-processing voltage application mode or the biological information measurement mode and modifies, according to the hematocrit value thus calculated, the duration for applying the measuring voltage upon and after the calculation of the hematocrit value. Thus, appropriate measurement can be carried out.

In other words, when the hematocrit value calculated is higher than the predetermined value, the variation in the biological information to be measured increases. Therefore, in order to reduce the variation, the duration for applying the measuring voltage is increased. In this way, the variation in the biological information to be measured can be reduced and as a result, appropriate measurement can be carried out.

Furthermore, when the hematocrit value calculated is lower than the predetermined value, the duration for applying the measuring voltage is reduced. In this way, the measurement time can be shortened and also in this case, appropriate measurement can be carried out.

Thus, it is expected to be used as, for example, a biological information detector for detecting biological information such as a blood glucose level.

DESCRIPTION OF THE NUMERALS

Body Case
2 Biosensor
3 Insertion Opening
4 Insulating Substrate
5 Blood Component Measurement Working Electrode
6 Blood Component Measurement Counter Electrode
7 Blood Component Introduction Detection Electrode
8 Input Terminal Portion
9 Reagent Portion
10 Reagent
11 Spacer
12 Cover
13 Blood Supply Path
14 Blood Supply Port
15 Air Hole
16 Voltage Applying Unit 17 Current-Voltage Conversion Part
18 Control Unit
19 A/D Conversion Part
20 Determination Means
21 Display Unit
22 Power Supply Unit
23 Memory Unit
24 Clock
25 Correction Means

The invention claimed is:

1. A biological information measurement device, to which a biosensor is attached, the biosensor comprising a first electrode and a second electrode, a reagent portion provided between the first electrode and the second electrode, and a guide portion for guiding blood to the reagent portion,
wherein the biological information measurement device comprises:
a first input terminal, to which the first electrode is connected, and a second input terminal, to which the second electrode is connected,
a voltage applying unit for applying a voltage to the first input terminal and the second input terminal, and
a control unit connected to the voltage applying unit, the control unit is configured to execute:
a pre-processing voltage application mode, in which the voltage applying unit applies a pre-processing voltage to the first input terminal and the second input terminal, and
a biological information measurement mode, in which after the pre-processing voltage application mode, the voltage applying unit applies a measuring voltage to the first input terminal and the second input terminal to measure biological information, and
the control unit has a configuration, in which the hematocrit value of the blood is calculated in either the pre-processing voltage application mode or the biological information measurement mode, and according to the hematocrit value thus calculated, the duration for applying the measuring voltage to the first input terminal and the second input terminal upon and after the calculation of the hematocrit value is modified.

2. The biological information measurement device according to claim 1, wherein the control unit has a configuration, in which when the hematocrit value calculated exceeds 55%, the control unit increases the duration for applying the measuring voltage in the biological information measurement mode as compared to the case where the hematocrit value is 55% or lower.

3. The biological information measurement device according to claim 1, wherein a third electrode is provided opposite to the guide portion for the first electrode and the second electrode, the third electrode is configured to be connected to a third input terminal of the biological information measurement device, the third input terminal is connected to the control unit, and the control unit executes a blood arrival detection mode, in which it is detected that the blood has reached the reagent portion prior to the pre-processing voltage application mode.

4. The biological information measurement device according to claim 1, further comprising a determination unit connected to the first input terminal and the second input terminal,
wherein the determination unit is connected to the control unit, and
the determination unit compares the current flowing between the first electrode and the second electrode with a threshold value through the first input terminal and the second input terminal.

5. A method of measuring biological information using a biological information measurement device according to claim 1,
wherein in either the pre-processing voltage application mode or the biological information measurement mode, the hematocrit value of the blood is calculated, and then according to the hematocrit value thus calculated, the duration for applying the measuring voltage upon and after the calculation of the hematocrit value is set.

6. A biological information measurement device, to which a biosensor is attached, the biosensor comprising a first electrode and a second electrode, a reagent portion provided between the first electrode and the second electrode, and a guide portion for guiding blood to the reagent portion,
wherein the biological information measurement device comprises:
a first input terminal, to which the first electrode is connected, and a second input terminal, to which the second electrode is connected,
a voltage applying unit for applying a voltage to the first input terminal and the second input terminal, and
a control unit connected to the voltage applying unit, the control unit is configured to execute:
a pre-processing voltage application mode, in which the voltage applying unit applies a pre-processing voltage to the first input terminal and the second input terminal,
a voltage application pause mode, in which after the pre-processing voltage application mode, the voltage applying unit pauses the voltage application to the first input terminal and the second input terminal, and
a biological information measurement mode, in which after the voltage application pause mode, the voltage applying unit applies a measuring voltage to the first input terminal and the second input terminal to measure biological information, and
the control unit has a configuration, in which the hematocrit value of the blood is calculated in an early stage of the biological information measurement mode and according to the hematocrit value thus calculated, the duration for applying the measuring voltage upon and after the calculation of the hematocrit value is modified.

7. The biological information measurement device according to claim 6, wherein the control unit has a configuration, in which when the hematocrit value calculated exceeds 55%, the control unit increases the duration for applying the measuring voltage in the biological information measurement mode as compared to the case where the hematocrit value is 55% or lower.

8. The biological information measurement device according to claim 6, wherein a third electrode is provided opposite to the guide portion for the first electrode and the second electrode, the third electrode is configured to be connected to a third input terminal of the biological information measurement device, the third input terminal is connected to the control unit, and the control unit executes a blood arrival detection mode, in which it is detected that the blood has reached the reagent portion prior to the pre-processing voltage application mode.

9. The biological information measurement device according to claim 6, further comprising a determination unit connected to the first input terminal and the second input terminal,
wherein the determination unit is connected to the control unit, and the determination unit compares the current flowing between the first electrode and the second electrode with a threshold value through the first input terminal and the second input terminal.

10. A method of measuring biological information using a biological information measurement device according to claim 6,
wherein a pre-processing voltage is applied to the first input terminal and the second input terminal from the voltage applying unit,
then the voltage application to the first input terminal and the second input terminal is paused,
thereafter, the measuring voltage is applied to the first input terminal and the second input terminal,
in an early stage of applying the measuring voltage, a hematocrit value of the blood is calculated, and
then according to the hematocrit value thus calculated, the duration for applying the measuring voltage upon and after the calculation of the hematocrit value is set.

* * * * *